US011596668B2

(12) United States Patent
Ferns et al.

(10) Patent No.: US 11,596,668 B2
(45) Date of Patent: Mar. 7, 2023

(54) TISSUE REPAIR (71) Applicant: THE UNIVERSITY OF SUSSEX, Brighton (GB)

(72) Inventors: Gordon Ferns, Brighton (GB); Lamia Heikal, Brighton (GB); Pietro Ghezzi, Brighton (GB)

(73) Assignee: The University of Sussex, Brighton (GB)

( * ) Notice: Subject to any disclaimer, the term of this patent is extended or adjusted under 35 U.S.C. 154(b) by 0 days.

(21) Appl. No.: 16/770,924

(22) PCT Filed: Dec. 6, 2018

(86) PCT No.: PCT/GB2018/053536
§ 371 (c)(1),
(2) Date: Jun. 8, 2020

(87) PCT Pub. No.: WO2019/110999
PCT Pub. Date: Jun. 13, 2019

(65) Prior Publication Data
US 2021/0162008 A1 Jun. 3, 2021

(30) Foreign Application Priority Data
Dec. 6, 2017 (GB) ..................................... 1720320

(51) Int. Cl.
| | | |
|---|---|---|
| A61K 38/18 | (2006.01) | |
| A61K 9/00 | (2006.01) | |
| A61K 9/70 | (2006.01) | |
| A61K 31/16 | (2006.01) | |
| A61K 31/225 | (2006.01) | |
| A61K 31/47 | (2006.01) | |
| A61K 31/4704 | (2006.01) | |
| A61K 31/4745 | (2006.01) | |
| A61K 33/24 | (2019.01) | |
| A61L 31/16 | (2006.01) | |
| A61P 17/02 | (2006.01) | |
| A61K 31/472 | (2006.01) | |

(52) U.S. Cl.
CPC ........ *A61K 38/1816* (2013.01); *A61K 9/0024* (2013.01); *A61K 9/7023* (2013.01); *A61K 31/16* (2013.01); *A61K 31/225* (2013.01); *A61K 31/47* (2013.01); *A61K 31/472* (2013.01); *A61K 31/4704* (2013.01); *A61K 31/4745* (2013.01); *A61K 33/24* (2013.01); *A61L 31/16* (2013.01); *A61P 17/02* (2018.01)

(58) Field of Classification Search
CPC .............. A61K 38/1816; A61K 9/0024; A61K 9/7023; A61K 31/16; A61K 31/225; A61K 31/47; A61K 31/4704; A61K 31/472; A61K 31/4745; A61K 33/24; A61K 31/164; A61K 31/223; A61K 45/06; A61L 31/16; A61L 2300/412; A61L 2300/416; A61L 15/44; A61P 17/02; A61P 9/10
See application file for complete search history.

(56) References Cited

U.S. PATENT DOCUMENTS

| | | |
|---|---|---|
| 2006/0276477 A1 | 12/2006 | Klaus et al. |
| 2010/0092546 A1 | 4/2010 | Gurtner et al. |
| 2010/0278916 A1 | 11/2010 | Bader |
| 2013/0197038 A1 | 8/2013 | Raghunath et al. |
| 2015/0320877 A1 | 11/2015 | Messersmith et al. |

FOREIGN PATENT DOCUMENTS

| | | |
|---|---|---|
| CN | 105999359 A | 10/2016 |
| WO | 2007/143211 A2 | 12/2007 |
| WO | 2009/035534 A2 | 3/2009 |
| WO | 2017/037655 A1 | 3/2017 |

OTHER PUBLICATIONS

Lakna, Difference between Epithelial and Endothelial Cells, PEDIAA, obtained online at: https://pediaa.com/difference-between-epithelial-and-endothelial-cells/, downloaded on Apr. 1, 2022. (Year: 2017).*
Heikal, Lamia et al., "Hypoxia enhances the regenerative effects of erythropoietin and its non-erythropoietic peptide analogue in models of endothelial cell injury", Sussex Research Online, Oct. 6, 2016.
Jones et al., "The role of HIF in cobalt-induced ischemic tolerance", Neuroscience, 252:420-430 (2013).
Heikal, Lamia et al., "Assessment of HIF-1α expression and release following endothelial injury in-vitro and in-vivo", Molecular Medicine, 24(1), pp. 1-10 (2018).
Duscher et al., "Transdermal deferoxamine prevents pressure-induced diabetic ulcers", PNAS, 112(1):94-99 (2015).
Chen et al., "Upregulating Hif-1α by hydrogel nanofibrous scaffolds for rapidly recruiting angiogenesis relative cells in diabetic wound", Advanced Healthcare Materials, 5(8):907-918 (2016).
Zhang et al., "Effects of dimethyloxalylglycine-embedded poly(ε-caprolactone) fiber meshes on wound healing in diabetic rats", Applied Materials & interfaces, 9:7950-7963 (2017).
Zhu et al., "Effects of dimethyloxalylglycine on wound healing of palatal mucosa in a rat model", BMC Oral Health, 15:1-8 (2015).
Porreca et al., "Antiproliferative effect of desferrioxamine on vascular smooth muscle cells in vitro and in vivo", Arteriosclerosis and Thrombosis, 14(2):299-304 (1994).
Shen et al., "Prolyl hydroxylase inhibitors increase neoangiogenesis and callus formation following femur fracture in mice", Journal of Orthopaedic Research, 27(10):1298-1305 (Oct. 2009).

(Continued)

*Primary Examiner* — Abigail Vanhorn
(74) *Attorney, Agent, or Firm* — Rodney J. Fuller; Booth Udall Fuller, PLC (57) ABSTRACT

The present invention relates to a hypoxia-inducible factor (HIF) activator, or a pharmaceutically acceptable salt or solvate thereof, for use in promoting tissue repair. The HIF activator, or the pharmaceutically acceptable salt or solvate thereof, is for use with a prototypical tissue-protective cytokine, or a pharmaceutically acceptable salt or solvate thereof, which is administered exogenously to the body being treated.

9 Claims, 9 Drawing Sheets

(56) References Cited

OTHER PUBLICATIONS

Marchbank et al., "Dimethyloxalylglycine stimulates the early states of gastrointestinal repair processes through VEGF-dependent mechanisms", Laboratory Investigation, 91:1684-1694 (Dec. 2011).
Urao et al., "Erythropoietin-mobilized endothelial progenitors enhance reendothelialization via Akt-endothelial nitric oxide synthase activation and prevent neointimal hyperplasia", Circulation Research, 98:1405-1413 (2006).
Search Report Under Section 17(5) for Application No. 1720320.9 dated Sep. 4, 2018 (7 pages).

* cited by examiner

1
TISSUE REPAIR

This application is the U.S. National Stage of International Application No. PCT/GB2018/053536, filed Dec. 6, 2018, which claims the benefit of and priority to Great Britain Application No. 1720320.9, filed Dec. 6, 2020, the contents of each of which are incorporated herein by reference in their entireties.

The present invention relates to tissue repair, and in particular to compounds for use in promoting tissue repair, particularly cell response to injury/wound repair. The invention extends to pharmaceutical compositions and methods of promoting tissue repair. The invention is especially concerned with preventing restenosis in patients who have undergone coronary angioplasty.

Atherosclerosis is a condition in which arteries become narrowed with plaques, or atheroma. If atherosclerosis restricts the flow of blood to the heart then this can cause angina, or myocardial infarction, if untreated. Medication may be used to treat the condition, but if this is ineffective, coronary angioplasty may then be required to restore the blood supply to the heart. This procedure uses a balloon to stretch the artery and, in most cases, a stent is left in place to hold the artery open. Over two million coronary angioplasties are performed worldwide each year.

Stenosis is the abnormal narrowing of a blood vessel leading to restricted blood flow, and restenosis is the recurrence of stenosis. Restenosis is observed in about 30% of patients having undergone coronary angioplasty over 3-5 years. Drug-eluting stents have been introduced to prevent restenosis. These stents are coated with anti-proliferative or immunosuppressive drugs that inhibit smooth muscle cell growth, and have reduced the incidence of restenosis to 10-15% over 5 years. However, a substantial rate of restenosis, or in-stent thrombosis (clotting) is still observed.

The present invention arises from the inventors' work in attempting to overcome the problems associated with the prior art.

The inventors have shown that hypoxia activates a repair switch that makes cells responsive to the reparative action of a prototypical tissue-protective cytokine, e.g. erythropoietin (EPO). Furthermore, they have also shown that this so-called "hypoxic priming" can be achieved at normal oxygen concentrations by administration of chemical inducers of the transcription factor HIF-1α. The inventors have also produced evidence that suggests that this triggering of the endothelial repair response can occur in vivo in a model of vascular injury. This suggests that local application of a HIF-1 inducer, and optionally a tissue-protective cytokine, for example by using a stent coated with these active agents, would promote wound repair and the repair of the endothelial lining following angioplasty. In vitro studies, and work in animal models has shown that endothelial repair can reduce the likelihood of restenosis and thrombosis.

Thus, in accordance with a first aspect of the invention, there is provided a hypoxia-inducible factor (HIF) activator, or a pharmaceutically acceptable salt or solvate thereof, for use in promoting tissue repair.

As described in the examples, the inventors have found that a HIF activator mimics some of the features of a low oxygen (hypoxia) environment. This activates a repair switch that makes cells responsive to the reparative action of a prototypical tissue-protective cytokine, such as EPO. Accordingly, a HIF activator promotes tissue repair, for instance see example 6 and FIG. 6. It may be appreciated that the term "tissue" relates to a biological tissue.

In one embodiment, promoting tissue repair may comprise promoting cell growth.

The HIF activator, or the pharmaceutically acceptable salt or solvate thereof, is preferably administered locally to the site where promotion of tissue repair is desired.

The HIF activator, or the pharmaceutically acceptable salt or solvate thereof, may be for use in promoting tissue repair in endothelial cells, epithelium cells and/or stem cells.

In one preferred embodiment, the HIF activator, or the pharmaceutically acceptable salt or solvate thereof, is for use in promoting tissue repair in endothelial cells, preferably vascular endothelial cells.

Accordingly, the HIF activator, or the pharmaceutically acceptable salt or solvate thereof, may be for use in preventing or reducing the likelihood of restenosis. The HIF activator, or the pharmaceutically acceptable salt or solvate thereof, may be administered locally to a blood vessel, for example a vein, an artery or a capillary. In a preferred embodiment the blood vessel is an artery, and more preferably a coronary artery. The HIF activator, or the pharmaceutically acceptable salt or solvate thereof may be administered to a coronary artery before, during or after angioplasty conducted on the coronary artery.

In an alternative preferred embodiment, the HIF activator, or the pharmaceutically acceptable salt or solvate thereof, is for use in promoting tissue repair in epithelial cells, preferably dermal epithelial cells. Accordingly, the HIF activator, or the pharmaceutically acceptable salt or solvate thereof, may be for use in promoting healing of a wound. The HIF activator, or the pharmaceutically acceptable salt or solvate thereof, may be administered locally to the wound.

In a further alternative embodiment, the HIF activator, or the pharmaceutically acceptable salt or solvate thereof, is for use in promoting tissue repair in stem cells, preferably in endothelial stem cells and more preferably in vascular endothelial stem cells. Accordingly, the HIF activator, or the pharmaceutically acceptable salt or solvate thereof, may be for use in regenerative medicine. The HIF activator, or the pharmaceutically acceptable salt or solvate thereof, may be administered locally.

The HIF activator, or the pharmaceutically acceptable salt or solvate thereof, is preferably a HIF-1 activator and/or a HIF-3 activator, or a pharmaceutically acceptable salt or solvate thereof. More preferably, the HIF activator, or the pharmaceutically acceptable salt or solvate thereof, is a HIF-1 activator, or a pharmaceutically acceptable salt or solvate thereof, and most preferably a HIF-1α activator, or a pharmaceutically acceptable salt or solvent thereof.

The HIF activator, or a pharmaceutically acceptable salt or solvate thereof, may be selected from a group consisting of: dimethyloxalylglycine (DMOG); N-[[1,2-Dihydro-4-hydroxy-2-oxo-1-(phenylmethyl)-3-quinolinyl]carbonyl]glycine (IOX); N-[(1-Chloro-4-hydroxy-3-isoquinolinyl)carbonyl]glycine (BIQ); desferrioxamine (DFX); 0-phenanthroline; iodochlorohydroxyquinoline; and cobalt chloride heptahydrate.

Preferably, the HIF activator, or a pharmaceutically acceptable salt or solvate thereof, is DMOG, IOX, BIQ or DFX. Most preferably, the HIF activator, or a pharmaceutically acceptable salt or solvate thereof, is DMOG or IOX.

The HIF activator, or the pharmaceutically acceptable salt or solvate thereof, may be administered without a prototypical tissue-protective cytokine. Accordingly, the HIF activator, or the pharmaceutically acceptable salt or solvate thereof, activates a repair switch that makes cells responsive to the reparative action of a prototypical tissue-protective cytokine which may be endogenously present in the body being treated, for instance see example 5 and FIG. 6 where application of DMOG alone showed a significant effect.

However, in a preferred embodiment, the HIF activator, or the pharmaceutically acceptable salt or solvate thereof, is for use with a prototypical tissue-protective cytokine, or a pharmaceutically acceptable salt or solvate thereof, which is administered exogenously to the body being treated. The prototypical tissue-protective cytokine, or the pharmaceutically acceptable salt or solvate thereof, may be administered before, simultaneously to, or after, the HIF activator, or the pharmaceutically acceptable salt or solvate thereof, is administered. In embodiments where the prototypical tissue-protective cytokine, or the pharmaceutically acceptable salt or solvate thereof, is administered before or after the HIF activator (or the pharmaceutically acceptable salt or solvate thereof) is administered, preferably both the prototypical tissue-protective cytokine (or the pharmaceutically acceptable salt or solvate thereof) and the HIF activator (or the pharmaceutically acceptable salt or solvate thereof) are administered in a sufficient quantity to ensure that physiologically active dosages of both are present at the same time in the body being treated.

Figure 4:
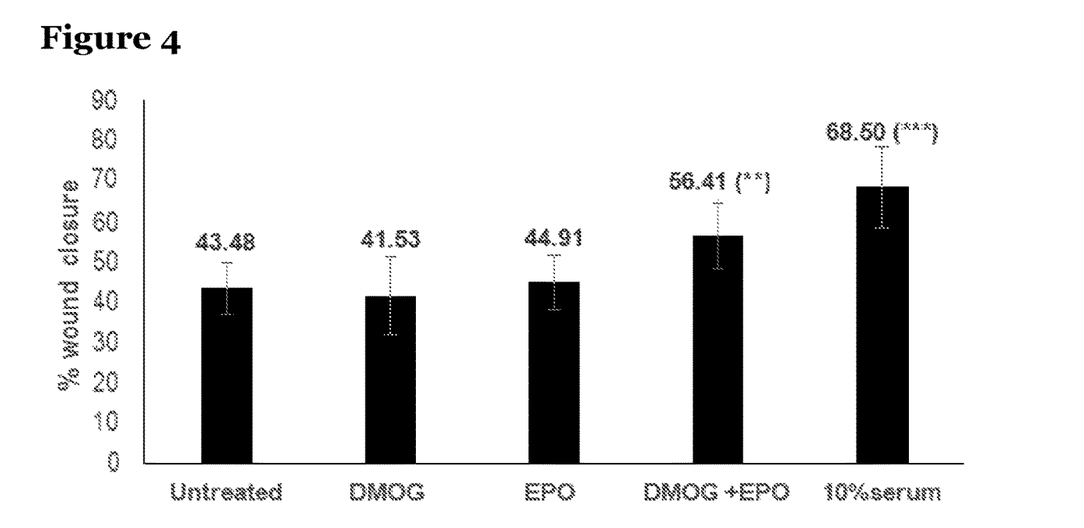
FIG. 4 is a graph showing the effects of erythropoietin (EPO, 1 ng/mL) and dimethyloxalylglycine (DMOG; 100 µM) on wound closure in a scratch assay model in rat aortic endothelial cells (RAECs) when incubated separately or together in cell culture medium containing 5% serum in 21% oxygen for 24 h. Results are expressed as % wound healing after 24 h. Each data point represents the mean value ±SEM (n=3). Different samples were tested for significant difference using one-way ANOVA where $p<0.01$, *$p<0.01$.
Figure 6:
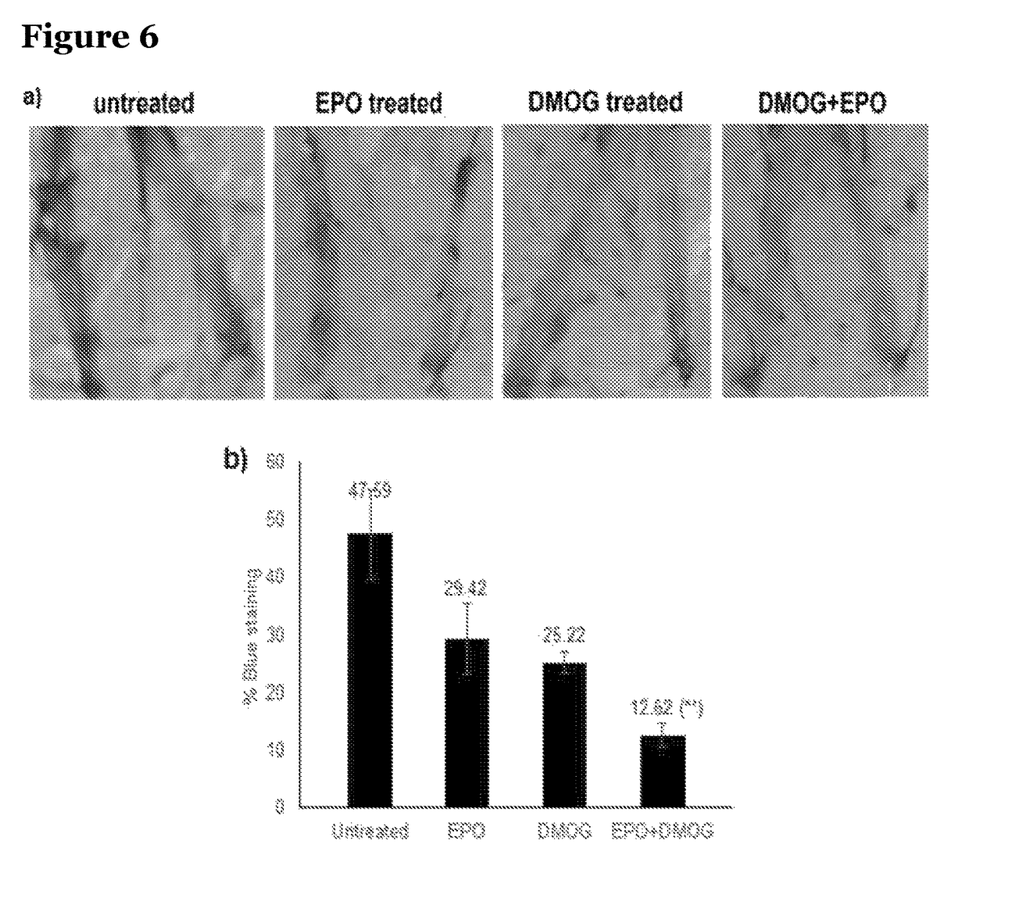
FIG. 6a shows representative images of rat carotid arteries after injury with balloon catheter (angioplasty) and treatment with erythropoietin (EPO, 100 µg/Kg) and dimethyloxalylglycine (DMOG, 5 mg/Kg), separately and in combination, applied locally on the left carotid artery using a hydrogel (30% w/v Pluronic acid gel) immediately after injury. Evans Blue (1% w/v) was used to assess the repair response; blue stained area represents de-endothelialised injured areas.
FIG. 6b is a graph showing quantitative analysis of the injured areas by measuring the blue stained 5 days post injury. Each data point represents mean±SEM (n=3). Different treatments were tested for significant difference using t-test where *$p<0.001$.
Figure 10:
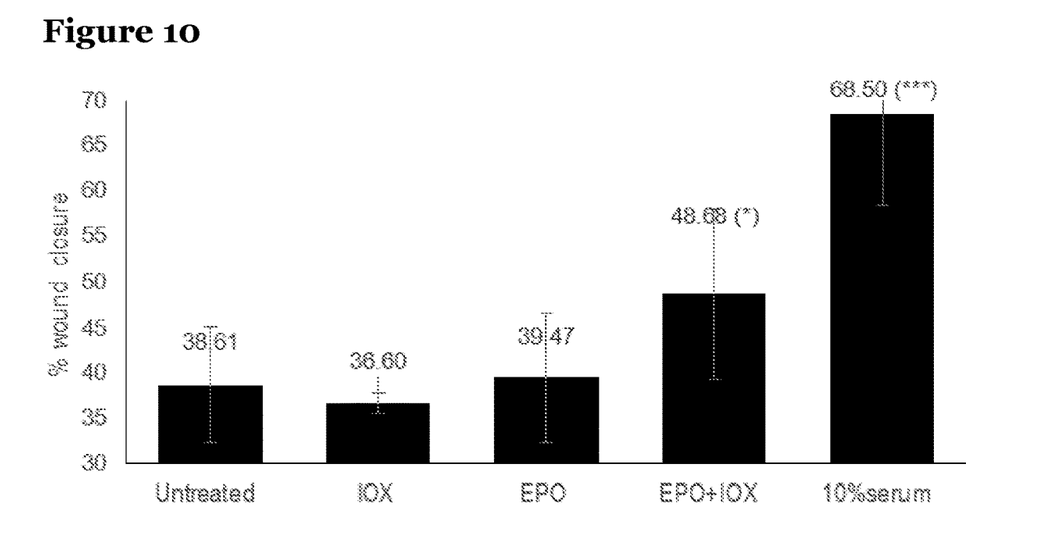
FIG. 10 shows how erythropoietin (EPO, 1 ng/mL) and N-[[1,2-Dihydro-4-hydroxy-2-oxo-1-(phenylmethyl)-3-quinolinyl]carbonyl]glycine (IOX, 100 µM) effected wound closure in a scratch assay model in rat aortic endothelial cells (RAECs) when incubated separately or together in cell culture medium containing 5% serum in 21% oxygen for 24 h. Results are expressed as % wound healing after 24 h. Each data point represents the mean value ±SEM (n=$_3$). Different samples were tested for significant difference using one-way ANOVA where p<0.01, *p<0.01.

Advantageously, the HIF activator, or the pharmaceutically acceptable salt or solvate thereof, activates a repair switch that makes cells responsive to the reparative action of the prototypical tissue-protective cytokine, or the pharmaceutically acceptable salt or solvate thereof, which has also been administered, for instance see examples 3, 5 and 7 and FIGS. 4, 6 and 10, which show a synergistic effect when a HIF activator is applied with a prototypical tissue-protective cytokine.

The prototypical tissue-protective cytokine, or the pharmaceutically acceptable salt or solvate thereof, is preferably administered locally to the site where promotion of tissue repair is desired.

The prototypical tissue-protective cytokine may be a member of the 4-alpha helical cytokine super family. Accordingly, the prototypical tissue-protective cytokine may be selected from the group consisting of: erythropoietin (EPO), interleukin 3 (IL-3), interleukin 5 (IL-5), interleukin 6 (IL-6), interleukin 11 (IL-11), leukaemia inhibitory factor (LIF) and a colony stimulating factors (CSF). Preferably, the prototypical tissue-protective cytokine is erythropoietin (EPO) or an analogue or derivative thereof.

It may be appreciated that a derivative of the prototypical tissue-protective cytokine may correspond to the structure of the prototypical tissue-protective cytokine but be modified at one or more amino acid residues. Preferably, the prototypical tissue-protective cytokine is EPO and the amino acid residue is a lysine residue.

The derivative of EPO may be a chemically modified EPO. Alternatively or additionally, the derivative of EPO may be desialylated EPO, carbamylated EPO (CEPO), asialoerythropoietin (asialo EPO), glutaraldehyde EPO (GEPO), epopeptide AB, an isoform of EPO or recombinant EPO. The derivative of EPO may be a derivative derived from recombinant EPO. The derivative of EPO and/or the recombinant EPO may be produced in a mammalian cell, an insect cell or in bacteria. The isoform of EPO may be EPO glycoform, as described in Mattio et al. ("Isolation and characterization of a subset of erythropoietin glycoforms with cytoprotective but minimal erythropoietic activity", Biotechnol Prog. 2011 July; 27(4):1018-28) or an isoform generated by alternative splicing, as described in Bonnas et al. ("EV-3, an endogenous human erythropoietin isoform with distinct functional relevance", Sci Rep. 2017 Jun. 16; 7(1):3684). Alternatively, or additionally, a derivative of EPO may be a mutant of EPO. The mutant of EPO may be EPO mutant S100E.

It may be appreciated that an analogue of EPO may mimic the tertiary structure of EPO. The analogue may be a synthetic analogue. Accordingly, the analogue of EPO may be pyroglutamate helix B surface peptide (pHBSP).

Pharmaceutically acceptable salts include any salt of a HIF activator and/or a prototypical tissue-protective cytokine provided herein which retains its biological properties and which is not toxic or otherwise undesirable for pharmaceutical use. The pharmaceutically acceptable salt may be derived from a variety of organic and inorganic counter-ions well known in the art.

The pharmaceutically acceptable salt may comprise an acid addition salt formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids. Alternatively, the pharmaceutically acceptable salt may comprise a base addition salt formed when an acidic proton present in the parent compound is either replaced by a metal ion, e.g., an alkali metal ion, an alkaline earth ion, an aluminium ion, alkali metal or alkaline earth metal hydroxides, such as sodium, potassium, calcium, magnesium, aluminium, lithium, zinc, and barium hydroxide, or coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

A pharmaceutically acceptable solvate refers to a HIF activator and/or a prototypical tissue-protective cytokine provided herein, or a salt thereof, that further includes a stoichiometric or non-stoichiometric amount of solvent bound by non-covalent intermolecular forces. Where the solvent is water, the solvate is a hydrate.

It will be appreciated that the HIF activator (or a pharmaceutically acceptable salt or solvate thereof), and optionally the prototypical tissue-protective cytokine (or a pharmaceutically acceptable salt or solvate thereof), described herein, may be used in a medicament which may be used in a monotherapy (i.e. use of the HIF activator, and optionally the prototypical tissue-protective cytokine, alone), for promoting tissue repair. Alternatively, the HIF activator, and optionally the prototypical tissue-protective cytokine, or a pharmaceutically acceptable salt or solvate thereof may be used as an adjunct to, or in combination with, known therapies for promoting tissue repair. Accordingly, the HIF activator, and optionally the prototypical tissue-protective cytokine, or a pharmaceutically acceptable salt or solvate thereof, may be used as an adjunct to, or in combination with, sirolimus, paclitaxel, zotarolimus or everolimus.

Known procedures, such as those conventionally employed by the pharmaceutical industry (e.g. in vivo experimentation, clinical trials, etc.), may be used to form specific formulations comprising the HIF activator, and optionally the prototypical tissue-protective cytokine, according to the invention and precise therapeutic regimes (such as daily doses of the HIF activator, and optionally the prototypical tissue-protective cytokine, and the frequency of administration). The inventors believe that they are the first to describe a pharmaceutical composition for promoting tissue repair, based on the use of the HIF activator, and optionally the prototypical tissue-protective cytokine, of the invention.

Hence, in a second aspect of the invention, there is provided a pharmaceutical composition for promoting tissue repair, the composition comprising a HIF activator, or a pharmaceutically acceptable salt or solvate thereof, and a pharmaceutically acceptable vehicle.

Preferably, the HIF activator, or the pharmaceutically acceptable salt or solvate thereof, is as described in relation to the first aspect.

Preferably, the composition also comprises a prototypical tissue-protective cytokine, or a pharmaceutically acceptable salt or solvate thereof. Preferably, the prototypical tissue-protective cytokine, or the pharmaceutically acceptable salt or solvate thereof, is as described in relation to the first aspect.

The pharmaceutical composition can be used to promote tissue repair in a subject. For example, the composition is most suitably used for treating or preventing restenosis or for facilitating wound healing, and for reducing scarring.

The invention also provides, in a third aspect, a method for making the composition according to the second aspect, the process comprising contacting a therapeutically effective amount of a HIF activator, or a pharmaceutically acceptable salt or solvate thereof, and a pharmaceutically acceptable vehicle.

Preferably, the method also comprises contacting the HIF activator, or the pharmaceutically acceptable salt or solvate thereof, and the pharmaceutically acceptable vehicle with a prototypical tissue-protective cytokine, or a pharmaceutically acceptable salt or solvate thereof.

The inventors believe that they are the first to have developed a pharmaceutical composition comprising both a HIF activator and also a prototypical tissue-protective cytokine, and used it in therapy.

Thus, in accordance with a fourth aspect, there is provided a pharmaceutical composition comprising: (i) a HIF activator, or a pharmaceutically acceptable salt or solvate thereof, (ii) a prototypical tissue-protective cytokine, or a pharmaceutically acceptable salt or solvate thereof, and (iii) a pharmaceutically acceptable vehicle, for use as a medicament.

Preferably, the HIF activator, or the pharmaceutically acceptable salt or solvate thereof, is as described in relation to the first aspect. Preferably, the prototypical tissue-protective cytokine, or the pharmaceutically acceptable salt or solvate thereof, is as described in relation to the first aspect.

A "subject" may be a vertebrate, mammal, or domestic animal. Hence, the HIF activator, and optionally the prototypical tissue-protective cytokine, according to the invention may be used to treat any mammal, for example livestock (e.g. a horse), pets, or may be used in other veterinary applications. Most preferably, however, the subject is a human being.

A "therapeutically effective amount" of the HIF activator, and optionally the prototypical tissue-protective cytokine, is any amount which, when administered to a subject, is the amount of drug that is needed to promote tissue repair.

For example, the therapeutically effective daily amount of the HIF activator, or a pharmaceutically acceptable salt or solvate thereof, used may be between 1 mg and 10000 mg or between 2 mg and 2000 mg, more preferably between 5 mg and 1000 mg or between 10 mg and 750 mg, and most preferably between 25 mg and 500 mg or between 50 mg and 500 mg. The therapeutically effective daily amount of the prototypical tissue-protective cytokine, or a pharmaceutically acceptable salt or solvate thereof, used may be between 0.1 mg and 100 mg or between 1 mg and 50 mg, more preferably between 2 mg and 25 mg or between 3 mg and 20 mg, and most preferably between 3 mg and 15 mg or between 4 mg and 10 mg.

Accordingly, the pharmaceutical composition for use as a medicament may comprise between 1 mg and 10000 mg of the HIF activator, or a pharmaceutically acceptable salt or solvate thereof, and between 0.1 mg and 100 mg of the prototypical tissue-protective cytokine, or a pharmaceutically acceptable salt or solvate thereof.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents (i.e. the HIF activator, and optionally the prototypical tissue-protective cytokine) according to the invention. In tablets, the HIF activator, and optionally the prototypical tissue-protective cytokine, may be mixed with a vehicle having the necessary compression properties in suitable proportions and compacted in the shape and size desired. The powders and tablets preferably contain up to 99% of HIF activator, and optionally the prototypical tissue-protective cytokine. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The HIF activator, and optionally the prototypical tissue-protective cytokine, according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intraocular, intravenous and particularly subcutaneous injection. The HIF activator, and optionally the prototypical tissue-protective cytokine, may be prepared as a sterile solid composition that may be dissolved or suspended at the time of administration using sterile water, saline, or other appropriate sterile injectable medium.

The HIF activator, and optionally the prototypical tissue-protective cytokine, and compositions of the invention may be administered in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The HIF activator, and optionally the prototypical tissue-protective cytokine, used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The HIF activator, and optionally the prototypical tissue-protective cytokine, may be provided in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising the HIF activator, and optionally the prototypical tissue-protective cytokine, described herein may be used in a number of ways. Compositions comprising the HIF activator, and optionally the prototypical tissue-protective cytokine, of the invention may be administered by inhalation (e.g. intranasally). The HIF activator, and optionally the prototypical tissue-protective cytokine, and compositions according to the invention may be administered to a subject by injection into the blood stream or directly into a site requiring treatment. Injections may be intravenous (bolus or infusion) or subcutaneous (bolus or infusion), or intradermal (bolus or infusion).

The HIF activator, and optionally the prototypical tissue-protective cytokine, may be administered orally. Accordingly, the HIF activator, and optionally the prototypical tissue-protective cytokine, may be contained within a composition that may, for example, be ingested orally in the form of a tablet, capsule or liquid.

Alternatively, the HIF activator, and optionally the prototypical tissue-protective cytokine, according to the invention may be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with the HIF activator, and optionally the prototypical tissue-protective cytokine, used according to the invention is required and which would normally require frequent administration (e.g. at least daily injection).

In a preferred embodiment, the HIF activator, and optionally the prototypical tissue-protective cytokine, may be incorporated into a stent.

Hence, in accordance with a fifth aspect, there is provided a stent comprising a HIF activator, or a pharmaceutically acceptable salt or solvent thereof.

Advantageously, the stent may be inserted during an angioplasty procedure and the HIF activator, or the pharmaceutically acceptable salt or solvate thereof, can be administered locally to a coronary artery thereafter, thereby preventing or reducing the likelihood of restenosis.

Preferably, the HIF activator, or the pharmaceutically acceptable salt or solvate thereof, is as described in relation to the first aspect.

Preferably, the stent also comprises a prototypical tissue-protective cytokine, or a pharmaceutically acceptable salt or solvent thereof. Preferably, the prototypical tissue-protective cytokine, or the pharmaceutically acceptable salt or solvate thereof, is as described in relation to the first aspect.

The stent may further comprise a known therapy for promoting tissue repair. Accordingly, the stent may further comprise sirolimus, paclitaxel, zotarolimus or everolimus.

Compositions may also be formulated for topical use. For instance, creams or ointments may be applied to the skin. Alternatively, the HIF activator, and optionally the prototypical tissue-protective cytokine, may be incorporated into a dressing which is configured to be applied to the skin.

In accordance with a sixth aspect, there is provided a topical formulation or a dressing configured to be applied to the skin, the formulation or dressing comprising a HIF activator, or a pharmaceutically acceptable salt or solvent thereof.

Advantageously, the topical formulation or the dressing may be applied directly to a wound. Thus, the dressing is preferably a wound dressing.

Preferably, the HIF activator, or the pharmaceutically acceptable salt or solvate thereof, is as described in relation to the first aspect.

Preferably, the topical formulation or the dressing also comprises a prototypical tissue-protective cytokine, or a pharmaceutically acceptable salt or solvent thereof. Preferably, the prototypical tissue-protective cytokine, or the pharmaceutically acceptable salt or solvate thereof, is as described in relation to the first aspect.

It will be appreciated that the amount of the HIF activator, and optionally the prototypical tissue-protective cytokine, that is required is determined by its biological activity and bioavailability, which in turn depends on the mode of administration, the physiochemical properties of the HIF activator, and optionally the prototypical tissue-protective cytokine, and whether it is being used as a monotherapy, or in a combined therapy. The frequency of administration will also be influenced by the half-life of the HIF activator, and optionally the prototypical tissue-protective cytokine, within the subject being treated. Optimal dosages to be administered may be determined by those skilled in the art, and will vary with the particular HIF activator, and optionally the particular prototypical tissue-protective cytokine, in use, the strength of the pharmaceutical composition, the mode of administration, and the extent to which promotion of tissue repair is desired. Additional factors depending on the particular subject being treated will result in a need to adjust dosages, including subject age, weight, gender, diet, and time of administration.

The daily dose of the HIF activator to be administered may be between 1 mg and 10000 mg or between 2 mg and 2000 mg, more preferably between 5 mg and 1000 mg or between 10 mg and 750 mg, and most preferably between 25 mg and 500 mg or between 50 mg and 500 mg.

In embodiments where it is present, the daily dose of the prototypical tissue-protective cytokine to be administered may be between 0.1 mg and 100 mg or between 1 mg and 50 mg, more preferably between 2 mg and 25 mg or between 3 mg and 20 mg, and most preferably between 3 mg and 15 mg or between 4 mg and 10 mg.

A patient receiving treatment may take a first dose upon waking and then a second dose in the evening (if on a two dose regime) or at 3- or 4-hourly intervals thereafter. Alternatively, a slow release device may be used to provide optimal doses of the HIF activator, and optionally the prototypical tissue-protective cytokine, according to the invention to a patient without the need to administer repeated doses.

In accordance with a seventh aspect, there is provided a method of promoting tissue repair in a subject, the method comprising administering to a subject in need of such treatment, a therapeutically effective amount of a HIF activator, or a pharmaceutically acceptable salt or solvate thereof.

Preferably, the method also comprises administering to the subject a therapeutically effective amount of a prototypical tissue-protective cytokine, or a pharmaceutically acceptable salt or solvate thereof.

Preferably, the HIF activator, or the pharmaceutically acceptable salt or solvate thereof, is as described in relation to the first aspect. Preferably, the prototypical tissue-protective cytokine, or the pharmaceutically acceptable salt or solvate thereof, is as described in relation to the first aspect.

All of the features described herein (including accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying drawings, in which:—

EXAMPLES

The inventors have explored the effects of a low oxygen environment on the response to a prototypical tissue-protective cytokine, e.g. erythropoietin (EPO), and how the effects of a low oxygen environment can be replicated in the body using HIF-1 activators.

Finally, the inventors have investigated the effects of applying a combination of a prototypical tissue-protective cytokine and a HIF-1 activator to a wound.

Example 1—Effect of Hypoxia on the Response to Erythropoietin (EPO)

Materials and Methods

Scratch assay: This assay was used as an in vitro model of injury in rat aortic endothelial cells (RAECs). The effect of EPO on wound closure was investigated in either 21% or 1% $O_2$. A reproducible scratch was produced in the endothelial monolayer and thereafter, either EPO (1 ng/mL) or saline (control) was added to the cells (in rat endothelial growth medium containing 5% serum) and subsequently incubated in 21% or 1% $O_2$ for 24 hours. The defined area of the scratch was photographed under an inverted microscope (Olympus CKX41; Olympus Corporation, Tokyo, Japan) at lox magnification using a Micropix 5 megapixel colour complementary metal-oxide semiconductor digital camera (Olympus Cooperation). The position of the wound image was standardized each time against a horizontal line drawn on the base of the plate passing through the centre of each well. The scratch area was quantified using ImageJ software (National institutes of Health, Bethesda, Md., USA).

Results

Figure 1:
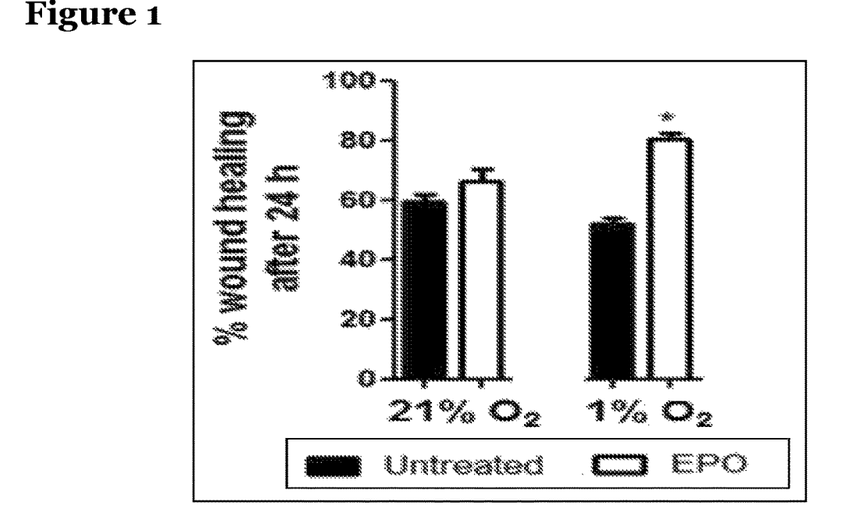
FIG. 1 is a graph showing the in vitro effects of erythropoietin (EPO) (1 ng/mL) on wound closure in aortic endothelial cells (BAECs) when incubated in 1% oxygen or 21% oxygen. Results are expressed as % wound healing after 24 h. Each data point represents the mean value ±SEM (n=6). Different samples were tested for significant difference using t-test where *$p<0.05$.

As shown in FIG. 1, the presence of EPO has little effect on wound healing when the cells are incubated under normal oxygen levels (21% oxygen). However, when the cells were incubated under a low oxygen level (1% oxygen), the presence of EPO was shown to significantly improve wound healing, both when compared to cells which were not treated with EPO and to cells treated with EPO and incubated under 21% oxygen.

The inventors hypothesised that hypoxia activates a molecular switch that makes cell responsive to the reparative effect of EPO. This could be due to activation of the adaptive response to low oxygen mediated by the transcription factor hypoxia-inducible factor-1 (HIF-1).

However, it will be appreciated that it is undesirable to lower oxygen concentration in patients. Accordingly, the inventors decided to see if this effect could be replicated using a HIF-1 activator, dimethyloxalylglycine (DMOG), as discussed in the further examples below.

Example 2—Determination of the Optimum Effective Concentration of a Standard HIF-1 Inducer, Dimethyloxalylglycine (DMOG), in Vitro Materials and Methods Cell culture: Rat aortic endothelial cells (RAECs) were seeded into 24-well plates and cultured until ~80% confluent after which they were incubated with or without DMOG for 18 h at normal oxygen levels (21% $O_2$). Cells incubated at 1% $O_2$ where used as a positive control for HIF-1.

Enzyme linked immunosorbent assay (ELISA): HIF-1 protein levels were measured using ELISA. Treated cells were lysed in 80 µL lysis buffer (25 mmol/L Tris HCl pH 7. 6, 0.1% SDS, deoxycholate, 1% NP40, 0.5 mol/L EDTA, 40 mmol/L EGTA and protease inhibitors). Lysates were then centrifuged at 11,000 g for 15 min at 4° C. and the supernatant was collected. Protein concentrations were quantified using a BCA reagent kit (Pierce Biotechnology). HIF was measured using an ELISA kit (R&D systems and biotechne, UK) and expressed as pg/mg protein.

Real time qPCR: The gene expression of vascular endothelial growth factor (VEGF), a HIF-1 target gene, was analysed by quantitative polymerase chain reaction (qPCR). Cells were lysed using TRIzol (Invitrogen, Life Technologies) and RNA was then extracted and purified. RNA quality and concentration were determined using a NanoDrop ND-1000 (NanoDrop Technologies). Reverse transcription and real-time quantitative PCR (qPCR) were carried out on RNA samples for VEGF and β2-microglobulin (a housekeeping gene not affected by change in oxygen levels), using TaqMan gene expression assays (Applied Biosystems/Life Technologies). For gene expression quantification, the comparative threshold cycle ($\Delta\Delta CT$) method was used following manufacturer's guide-lines. Results were normalized to β2-microglobulin expression and expressed as arbitrary units using one of the normoxic untreated samples as a calibrator.

Viability assay: Cell viability was evaluated using MIT viability assay. Cells were seeded into 96-well plates at a density of $1\times10^5$ cells/mL (0.15 mL/well) in culture medium. After 24 h, medium was removed and replaced by 150 µL fresh medium containing different concentrations of DMOG (0-500 µM) and incubated for 0 and 24 h. At each time point, MTT reagent was added, incubated for 3 hours. Formazan crystals formed only from living cells where then dissolved in DMSO and absorbance was measured at wavelength 540 and 630 nm. Results were expressed as number of cells/mL.

Results

Figure 2:
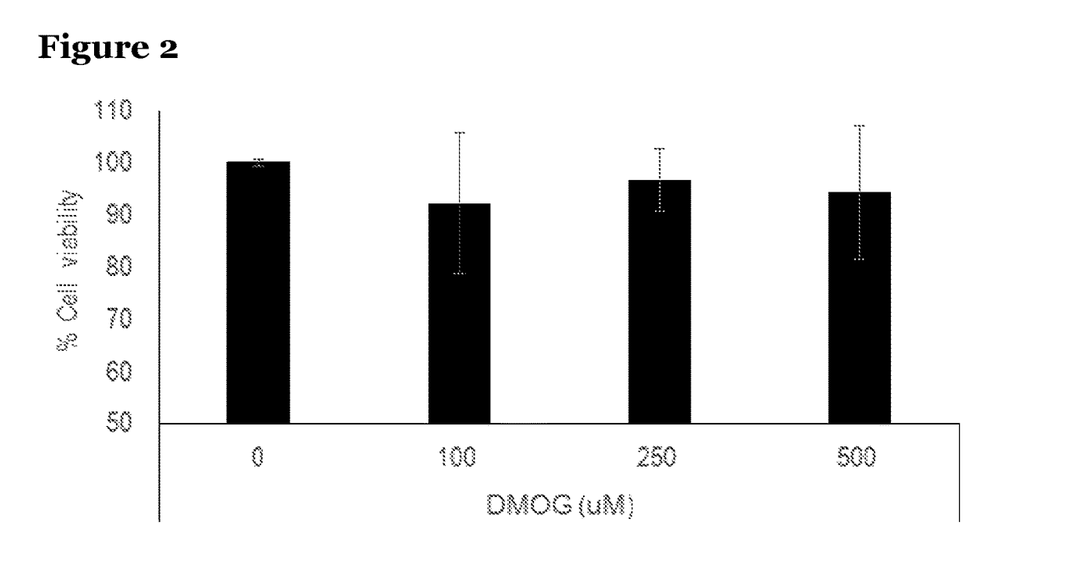
FIG. 2 is a graph showing the cell viability of rat aortic endothelial cells (RAECs) is not affected when exposed to different concentrations of dimethyloxalylglycine (DMOG) between 0-500 µM. Each data represents the mean value ±SEM (n=3). Different samples were tested for significance difference using t-test.

As shown in FIG. 2, DMOG was not toxic to rat aortic endothelial cells (RAECs) when used in concentrations of up to 500 µM.

Figure 3:
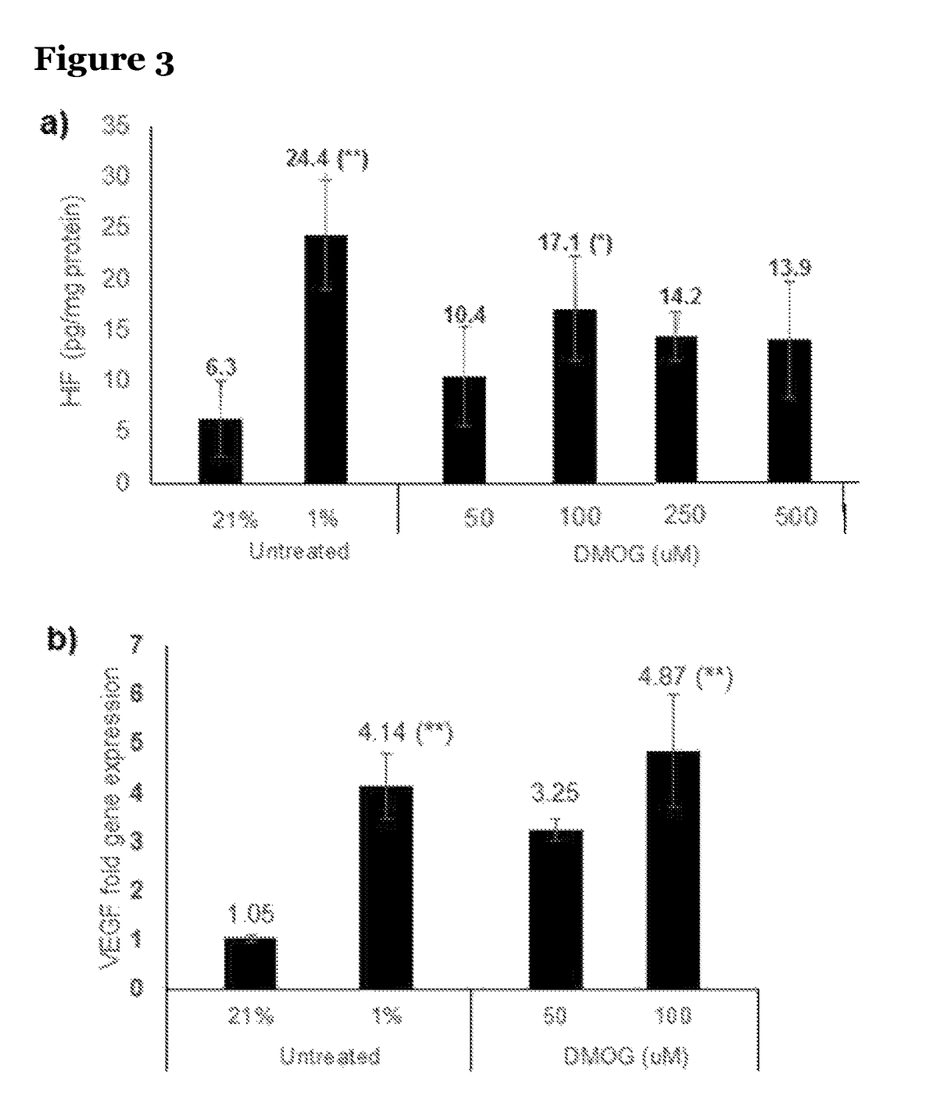
FIG. 3 is a graph showing the effect of different concentrations of dimethyloxalylglycine (DMOG) on a) hypoxia inducible factor-1 (HIF-1) levels in cell lysates from rat aortic endothelial cells and b) gene expression of vascular endothelial growth factor (VEGF), one of the proteins whose production is regulated by HIF. Each data represents the mean value ±SEM (n=3), different samples were tested for significant difference using t-test where *$p<0.05$, **$p<0.01$.

As shown in FIG. 3, a concentration of 100 µM of DMOG was found to increase the HIF levels and gene expression of vascular endothelial growth factor (VEGF), one of the downstream effectors of HIF, in cell lysates from rat aortic endothelial cells to a level which is similar to that observed for cells incubated at low oxygen levels (1% oxygen).

Example 3—In Vitro Study of Effect of Combination of DMOG and EPO

Materials and Methods

Scratch assay: Scratch assay was used as described in example 1. Cells where treated with DMOG (100 μM) and/or EPO (at 1 ng/mL). Cells incubated with medium containing 10% serum where used as positive control to reflect the maximum wound closure the cells could attain after 24 h.

Results

As shown in FIG. 4, when cells were treated with just 100 μM of DMOG or just 1 ng/ml of EPO the % wound closure is similar to that observed for untreated cells.

However, when cells were treated with a combination of 100 μM of DMOG and 1 ng/ml of EPO then a significant improvement was observed getting close to the maximum wound closure the cells could get to after 24 h.

Example 4—Determination of the Optimum Effective DMOG Concentration in Vivo

Materials and Methods

Male animal study: Sprague Dawley rats (450 g) were used in this study. Animals were anesthetized using 2% isoflurane where the rats were placed in a supine position. The right carotid artery was exposed and DMOG was applied locally at different concentrations (0-7.5 mg/Kg) on the artery using pluronic gel (30% w/w). 3 rats were used in each concentration group.

ELISA: After 24 h, blood was taken from the rat's tail in tubes containing EDTA as an anti-coagulant. Blood was kept on ice and centrifuged to separate the plasma which was immediately treated with a protease inhibitor. HIF-1 was quantified in the collected plasma using the ELISA assay as described in example 2. After 24 h, treated animals were culled and both the right (treated) and left (untreated) carotid arteries were isolated and snap frozen for further analysis.

Real time qPCR: RNA was extracted and purified from the frozen artery sections using TRIzol (Invitrogen, Life Technologies). RNA quality and concentrations were determined using a NanoDrop ND-1000 (NanoDrop Technologies). Reverse transcription and real-time quantitative PCR (qPCR) were carried out on RNA samples for VEGF and β2-microglobulin as described in example 2.

Results

Figure 5:
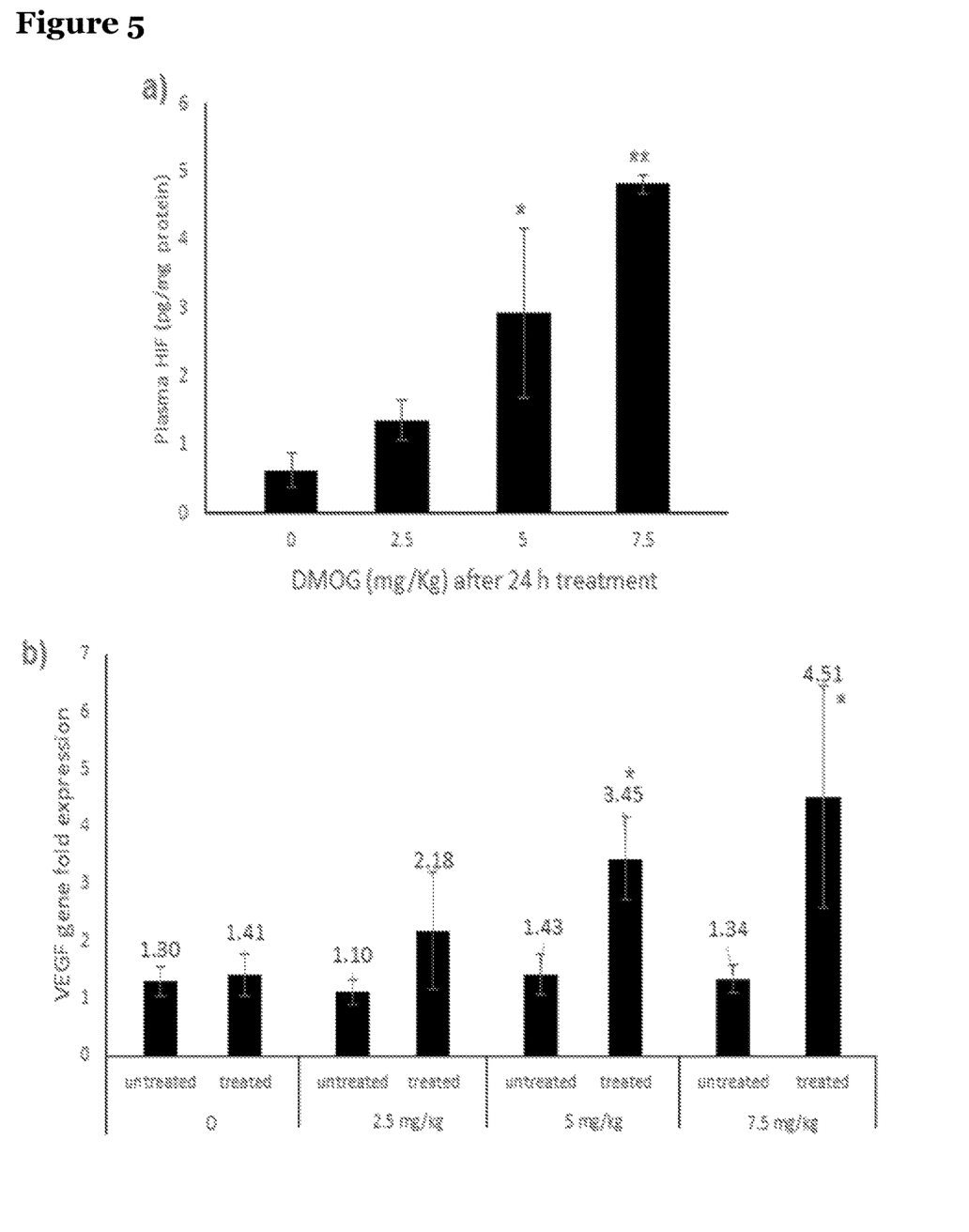
FIG. 5 is a graph showing the effect different concentrations of dimethyloxalylglycine (DMOG) had on a) hypoxia inducible factor-1 (HIF-1) levels in plasma and b) gene expression of vascular endothelial growth factor (VEGF) in carotid artery. Each data represents the mean value ±SEM (n=$_3$), different samples were tested for significant difference using t-test where *$p<0.05$, **$p<0.01$.

As shown in FIG. 5, the inventors observed that DMOG showed a concentration dependent effect on increasing HIF levels in plasma and increasing gene expression of VEGF. The inventors identified that the optimal dose of DMOG to cause an increase in HIF-1 and VEGF as 5 mg/kg.

Example 5—In Vivo Study of Effect of Combination of DMOG and EPO

Materials and Methods

Angioplasty model: Balloon catheter injury (angioplasty) was the model used as an in vivo injury model using Sprague Dawley rats (450 g). Animals were anesthetized using 2% isoflurane where the rats were placed in a supine position. The right carotid artery was exposed and a (2F Fogarty catheter) was used to cause injury. The catheter was inserted into the common carotid artery via the external carotid to cause complete removal of the vascular endothelium from the common carotid artery down to its junction with the aortic arch. DMOG (5 mg/Kg) and EPO (100 ug/Kg) were administered either alone or in combination in the form of a hydrogel (30% w/v pluronic F127 gel) and applied to the artery after injury. Endothelial regrowth was then assessed using Evan's blue staining (injected IV in the tail vein 30 min before culling the animal) 0 and 5 days after injury to assess the area of de-endothelialised surface; re-endothelialised regions remain unstained. Images of stained arteries were quantified using Image J software.

ELISA: Blood was collected from venous tail at 0, 1 and 5 days post injury. Plasma was separated and used for quantitative measurement of HIF-1 using ELISA method as described earlier.

Results

As shown in FIG. 6, the repair of the endothelial lining of rat carotid artery 5 days after injury was much improved by the combination of DMOG and EPO compared to either drug when used alone.

Figure 7:
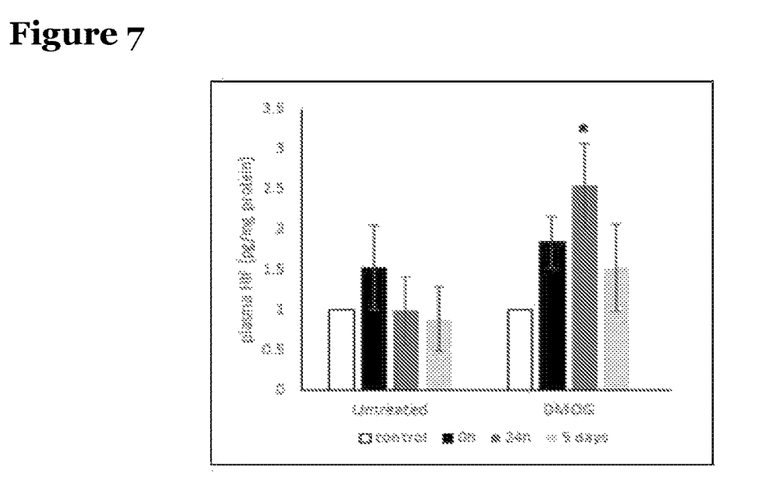
FIG. 7 is a graph showing hypoxia inducible factor (HIF) levels in plasma taken from rats at 0, 1 and 5 days post injury using an ELISA kit. Each data point represents mean±SEM (n=3). Different treatments were tested for significant difference using one-way ANOVA where *$p<0.001$ compared to arteries immediately after injury.

Furthermore, the inventors noted that DMOG significantly increased HIF-1 levels in rat plasma 24 h post injury, see FIG. 7.

Example 6—Determination of the Optimum Effective Concentration of Alternative HIF Inducers in Vitro Materials and Methods Different HIF inducers were purchased from Sigma Aldrich (Dorset, UK):
1. BIQ: N-[(1-Chloro-4-hydroxy-3-isoquinolinyl)carbonyl] glycine
2. IOX: N-[[1,2-Dihydro-4-hydroxy-2-oxo-1-(phenylmethyl)-3-quinolinyl]carbonyl]-glycine
3. DFX: Desferrioxamine Similar to the methods described in example 2, HIF-1 protein expression and VEGF gene expression were quantitatively measured in vitro using ELISA and real time qPCR respectively using different the different HIF-1 inducers at different concentrations (0-500 uM).

Viability test: Effect of different HIF-1 inducers on cell viability was tested at different concentrations (0-500 μM) using MTT method as described previously in example 2.

Results

Figure 9:
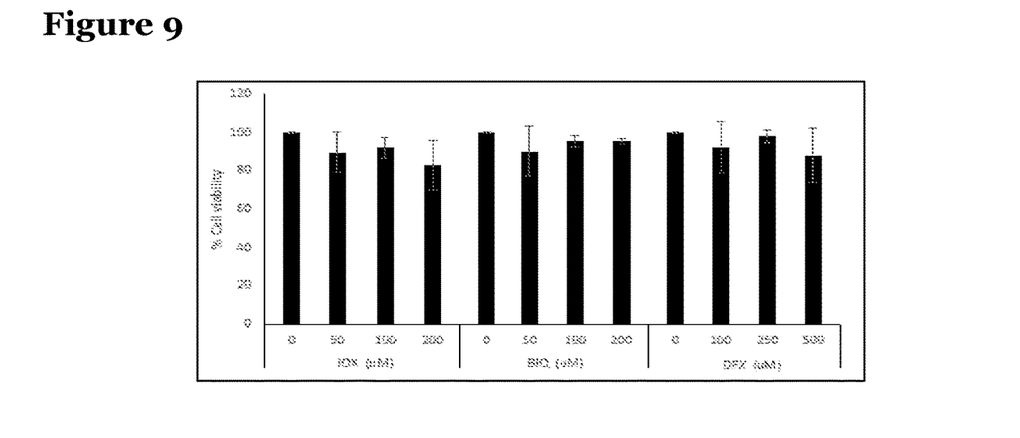
FIG. 9 shows the cell viability of rat aortic endothelial cells (RAECs) exposed to different hypoxia inducible factor (HIF) inducers: N-[[1,2-Dihydro-4-hydroxy-2-oxo-1-(phenylmethyl)-3-quinolinyl]carbonyl]glycine (IOX), N-[(1-Chloro-4-hydroxy-3-isoquinolinyecarbonyl]glycine (BIQ) or desferrioxamine (DFX) at concentrations ranging from 0-200 µM. Each data represents the mean value ±SEM (n=3)

As shown in FIG. 9, none of the HIF inducers used were toxic to rat aortic endothelial cells (RAECs) when used in concentrations of up to 500 μM.

Figure 8:
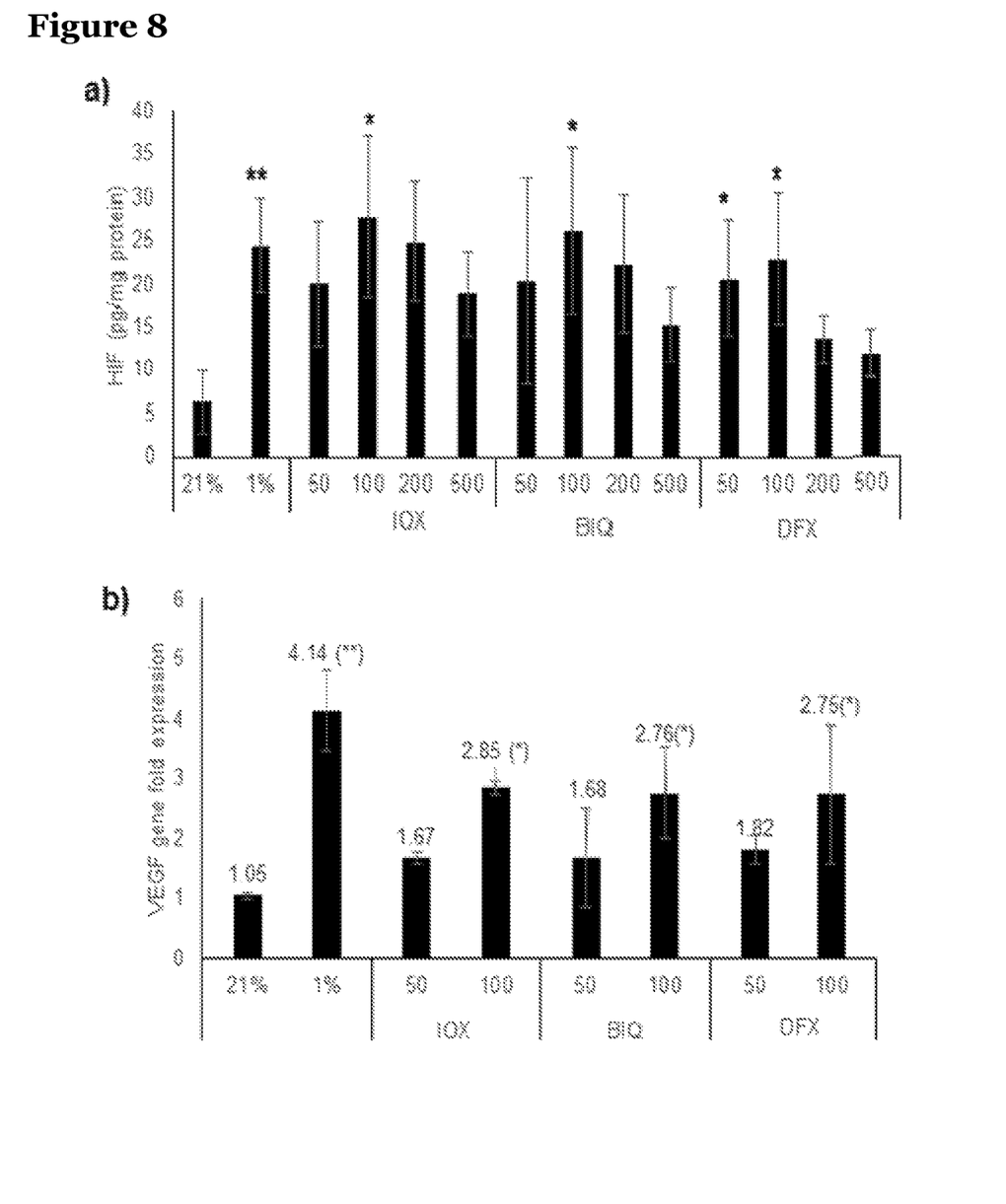
FIG. 8 shows the effect different concentrations of several hypoxia inducible factor-1 (HIF-1) inducers: N-[[1,2-Dihydro-4-hydroxy-2-oxo-1-(phenylmethyl)-3-quinolinyl]carbonyl]glycine (IOX), N-[(1-Chloro-4-hydroxy-3-isoquinolinyl)carbonyl]glycine (BIQ) or desferrioxamine (DFX) had on a) HIF levels in cell lysates from rat aortic endothelial cells and b) gene expression of vascular endothelial growth factor (VEGF). Each data represents the mean value ±SEM (n=$_3$), different samples were tested for significant difference using t-test where *$p<0.05$, **$p<0.01$.

As shown in FIG. 8, a concentration of 100 μM was the optimum concentration for all of the HIF-1 inducers to increase the HIF levels and gene expression of vascular endothelial growth factor (VEGF) in cell lysates from rat aortic endothelial cells to a level which is similar to that observed for cells incubated at low oxygen levels (1%).

Example 7—In Vitro Study of Effect of Combination of IOX and EPO

Materials and Methods

Scratch assay: Similar to example 3, the reparative effect of EPO (1 ng/mL) and the HIF-1 inducer; IOX (100 uM) were tested either alone or in combination in an in vitro scratch injury model.

Results

As shown in FIG. 10, no change was observed when cells were treated with just 100 μM of IOX or just 1 ng/ml of EPO when compared to untreated cells. However, when cells were treated with a combination of 100 μM of IOX and 1 ng/ml of EPO, a significant improvement was observed compared to the maximum closure the cells could achieve when incubated with 10% serum.

Example 8—Effect of HIF Inducers on Proliferation of Endothelial Cells and Smooth Muscle Cells Materials and Methods Proliferation assay: Proliferation of rat aortic endothelial cells (RAECs) and rat aortic smooth muscle cells (isolated from rats at animal unit at Sussex University) was evaluated using Trypan Blue exclusion test. Cells were seeded in 96 well plates at a seeding density of $1 \times 10^4$ cells/mL (0.15 mL/well). After 24 h, cells where treated with or without different concentrations of 2 HIF-1 inducers; DMOG and BIQ (0-200 µM). After another 24 hours, Trypan Blue was added and the cells that were stained (dead) and unstained (live) were counted. Results were expressed as number of cells/mL.

Results

Figure 11:
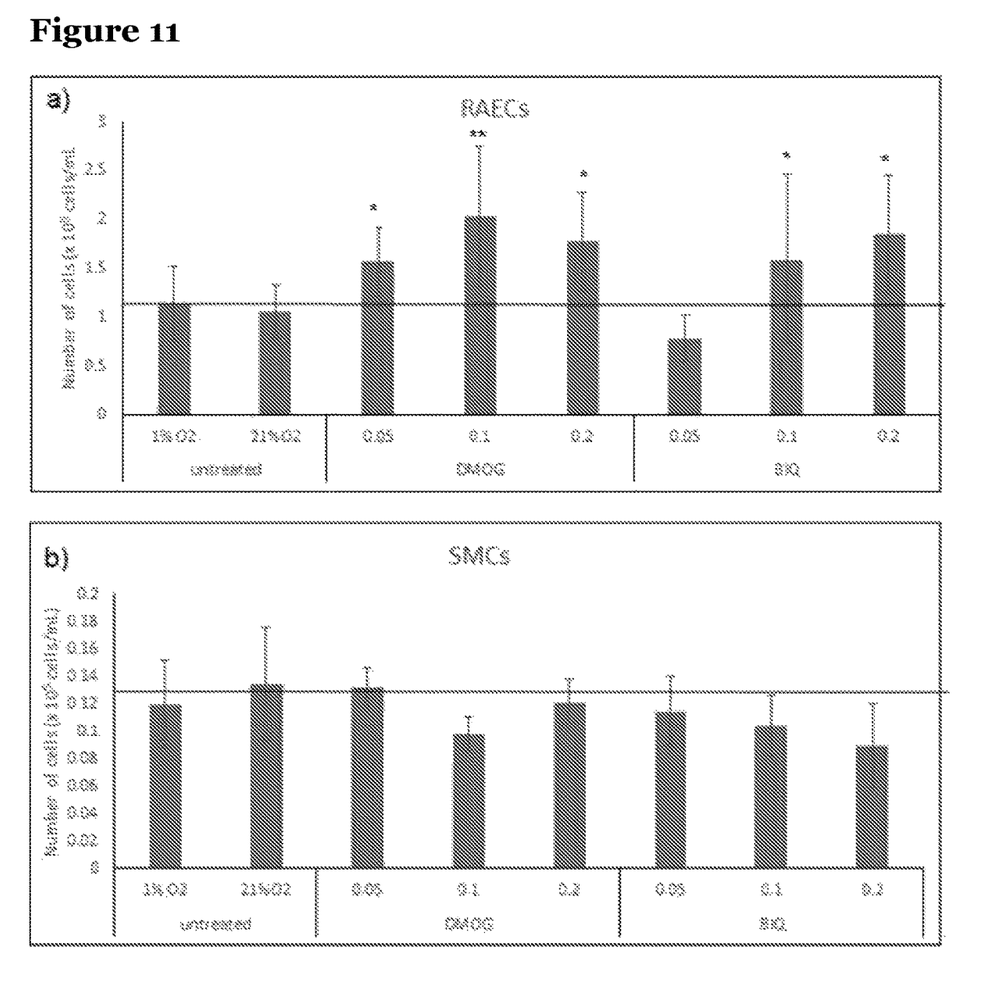
FIG. 11 shows how different hypoxia inducible factor (HIF) inducers: dimethyloxalylglycine (DMOG) and N-[(1-Chloro-4-hydroxy-3-isoquinolinyecarbonyl]glycine (BIQ) a) enhanced the proliferation of rat aortic endothelial cells (RAECs) at the concentrations 0.1 mM but b) had no effect on the proliferation of rat aortic smooth muscle cells (SMCs). Effect of different HIF inducers on cell proliferation was done using MIT test. Each data represents the mean value ±SEM (n=3), different samples were tested for significant difference using t-test, *p<0.05 and **p<0.01.

As shown in FIG. 11, the 2 HIF-1 inducers DMOG and BIQ enhanced the proliferation of rat aortic endothelial cells at an optimum concentration of 100 µM. The same HIF-1 inducers had no effect on the proliferation of smooth muscle cells at the concentrations used.

Example 9—In Vitro Study of Effect of Combination of DMOG and EPO on Skin Cells Materials and Methods An in vitro injury model using cells relevant to wound injury were used. Two different cell lines; human keratinocytes (HaCaT) and human fibroblasts were used as skin injury models.

Scratch assay: As described in example 3, the reparative effect of EPO (1 ng/mL) and DMOG (100 uM) were tested alone or in combination on HaCaT and fibroblasts incubated in cell culture medium (Dulbeccos cell culture medium) containing 3% serum in 21% oxygen for 24 h.

Results

Figure 12:
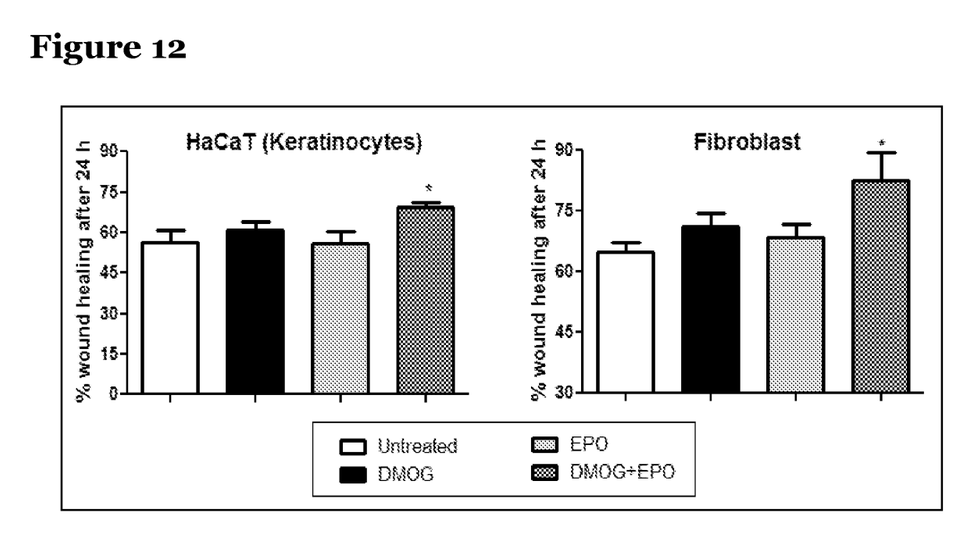
FIG. 12 shows how dimethyloxalylglycine (DMOG) primes the reparative effect of erythropoietin (EPO) in a scratch assay model in human keratinocyte cells (HaCaT) and Human fibroblast cells. EPO (1 ng/mL) and DMOG (100 µM) enhanced wound closure in HaCaT and fibroblasts when incubated together in cell culture medium containing 3% serum in 21% oxygen for 24 h. Results are expressed as % wound healing after 24 h. Each data point represents the mean value ±SEM (n=3), *p<0.05.

As shown in FIG. 12, similar to the results obtained with endothelial cells, there was no significant different in % wound closure when human fibroblasts and keratinocyte cells were treated with just 100 µM of DMOG or just 1 ng/ml of EPO compared to untreated cells. However, when cells were treated with a combination of 100 µM of DMOG and 1 ng/ml of EPO, a significant improvement was observed in the % wound closure.

CONCLUSIONS

The inventors have shown that low oxygen (hypoxia) activates a repair switch that makes cells responsive to the reparative action of a prototypical tissue-protective cytokine (TPCs), e.g. EPO. Furthermore, this priming can be achieved at normal oxygen concentrations by administration of chemical inducers of the transcription factor HIF-1α. The inventors have also produced evidence that suggests that this triggering of the endothelial repair response can occur in vivo in a model of vascular injury. This suggests that local application of a HIF-1 inducer and tissue-protective cytokines, such as by using a coated stent, could promote wound repair and promote the repair of the endothelial lining post-angioplasty.

The inventors have shown that HIF-1 inducers in combination with TPCs enhance the proliferation of endothelial cells with no effect on smooth muscle cells. This is very important in terms of retarding the process of restenosis.

The inventors have also shown that the combination of the prototypic TPC; EPO and the HIF-1 inducer; DMOG not only works in injury models of the endothelial cells but also works on injury models of skin cells. This is very promising as the same approach could be extended to wound healing as well as cardiovascular disease.

The invention claimed is:

1. A method of promoting tissue repair in dermal epithelial cells in a subject, the method comprising administering to a subject in need thereof a synergistic combination of (a) a therapeutically effective amount of a hypoxia-inducible factor (HIF) activator, or a pharmaceutically acceptable salt or solvate thereof, and (b) a therapeutically effective amount of a prototypical tissue-protective cytokine, or a pharmaceutically acceptable salt or solvate thereof, wherein the HIF activator of the pharmaceutically acceptable salt or solvate thereof is administered exogenously to the body of the subject being treated, wherein the HIF activator, or a pharmaceutically acceptable salt or solvate thereof, is selected from a group consisting of: dimethyloxalylglycine (DMOG); N-[[1,2-Dihydro-4-hydroxy-2-oxo-1-(phenylmethyl)-3-quinolinyl]carbonyl] glycine (IOX); N-[(1-Chloro-4-hydroxy-3-isoquinolinyl)carbonyl]glycine (BIQ); desferrioxamine (DFX); o-phenanthroline; iodochlorohydroxyquinoline; and cobalt chloride heptahydrate and the prototypical tissue-protective cytokine is erythropoietin (EPO) or an analogue or derivative thereof.

2. The method according to claim 1, wherein the HIF activator, or the pharmaceutically acceptable salt or solvate thereof, is administered locally to the site where promotion of tissue repair is desired.

3. The method according to claim 1, wherein the method is a method of promoting wound healing.

4. The method according to claim 1, wherein the HIF activator, or the pharmaceutically acceptable salt or solvate thereof, is a HIF-1 activator and/or a HIF-3 activator, or a pharmaceutically acceptable salt or solvate thereof.

5. The method according to claim 4, wherein the HIF activator, or the pharmaceutically acceptable salt or solvate thereof, is a HIF-1 activator, or a pharmaceutically acceptable salt or solvate thereof.

6. The method according to claim 5, wherein the HIF activator, or the pharmaceutically acceptable salt or solvate thereof, is a HIF-1α activator, or a pharmaceutically acceptable salt or solvent thereof.

7. The method according to claim 1, wherein the analogue or derivative of EPO is desialylated EPO, carbamylated EPO (CEPO), asialoerythropoietin (asialoEPO), glutaraldehyde EPO (GEPO), epopeptide AB, an isoform of EPO, recombinant EPO, mutant S100E of EPO or pyroglutamate helix B surface peptide (pHBSP).

8. The method according to claim 1, wherein the HIF activator or a pharmaceutically acceptable salt or solvate thereof, is dimethyloxalylglycine (DMOG) or N-[[1,2-Dihydro-4-hydroxy-2-oxo-1-(phenylmethyl)-3-quinolinyl] carbonyl] glycine (IOX).

9. The method according to claim 1, wherein the prototypical tissue-protective cytokine is erythropoietin (EPO).

* * * * *